(12) United States Patent
Friend et al.

(10) Patent No.: US 8,551,041 B2
(45) Date of Patent: Oct. 8, 2013

(54) NAVIGABLE SYSTEM FOR CATHETER BASED ENDOVASCULAR NEUROSURGERY

(75) Inventors: James Friend, Victoria (AU); Leslie Yeo, Victoria (AU); Bernard Yan, Toorak (AU)

(73) Assignee: Royal Melbourne Institute of Technology, Melbourne, Victoria (AU)

( * ) Notice: Subject to any disclaimer, the term of this patent is extended or adjusted under 35 U.S.C. 154(b) by 0 days.

(21) Appl. No.: 13/393,644

(22) PCT Filed: Sep. 3, 2010

(86) PCT No.: PCT/AU2010/001136
§ 371 (c)(1),
(2), (4) Date: Jun. 14, 2012

(87) PCT Pub. No.: WO2011/026187
PCT Pub. Date: Mar. 10, 2011

(65) Prior Publication Data
US 2012/0289897 A1 Nov. 15, 2012

(30) Foreign Application Priority Data
Sep. 3, 2009 (AU) ................................ 2009904281

(51) Int. Cl.
*A61M 31/00* (2006.01)
(52) U.S. Cl.
USPC ......... 604/95.01; 310/326; 310/366; 310/367
(58) Field of Classification Search
CPC .................................................... A61M 31/00
USPC ........................ 310/326, 328, 366; 604/95.01
See application file for complete search history.

(56) References Cited

U.S. PATENT DOCUMENTS

| 5,501,228 A * | 3/1996 | Lafontaine et al. ........... 600/505 |
| 2005/0119679 A1 * | 6/2005 | Rabiner et al. ................ 606/159 |
| 2006/0025719 A1 * | 2/2006 | Viswanathan et al. ..... 604/95.01 |
| 2007/0244423 A1 * | 10/2007 | Zumeris et al. ................. 604/22 |
| 2007/0265551 A1 * | 11/2007 | Pfister ........................... 600/585 |
| 2010/0320869 A1 * | 12/2010 | Li et al. .................... 310/323.02 |

FOREIGN PATENT DOCUMENTS

| WO | WO 95/04556 | 2/1995 |
| WO | WO 01/80922 | 11/2001 |
| WO | WO 2005/082441 | 9/2005 |
| WO | WO 2011/026187 | 3/2011 |

* cited by examiner

*Primary Examiner* — Nicholas Lucchesi
*Assistant Examiner* — Gerald Landry, II
(74) *Attorney, Agent, or Firm* — Woodcock Washburn LLP

(57) ABSTRACT

A navigable system for catheter based endovascular neurosurgery including: a micro-motor (3) including a piezoelectric actuator (5) mounted to a free end of a guidewire or micro-catheter (2), the piezoelectric actuator (5) including a piezoelectric element (7), and an elongate transducer (9) mounted on the piezoelectric element (7) and extending therefrom, the transducer (9) being formed from an asymmetric hollow member, and an end member (15) located at a free end of the transducer (9); wherein electrical excitation of the piezoelectric element (7) induces one or both orthogonal flexural and axial vibration modes within the transducer (9), the coupling of the induced vibration modes thereby resulting in rotation of the end member (15) with three degrees of freedom (DOF).

7 Claims, 2 Drawing Sheets

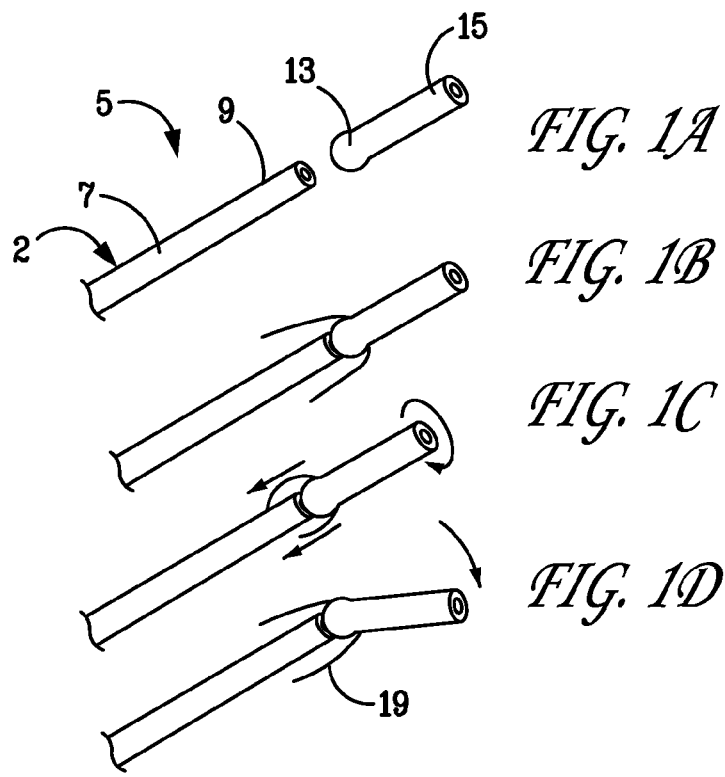
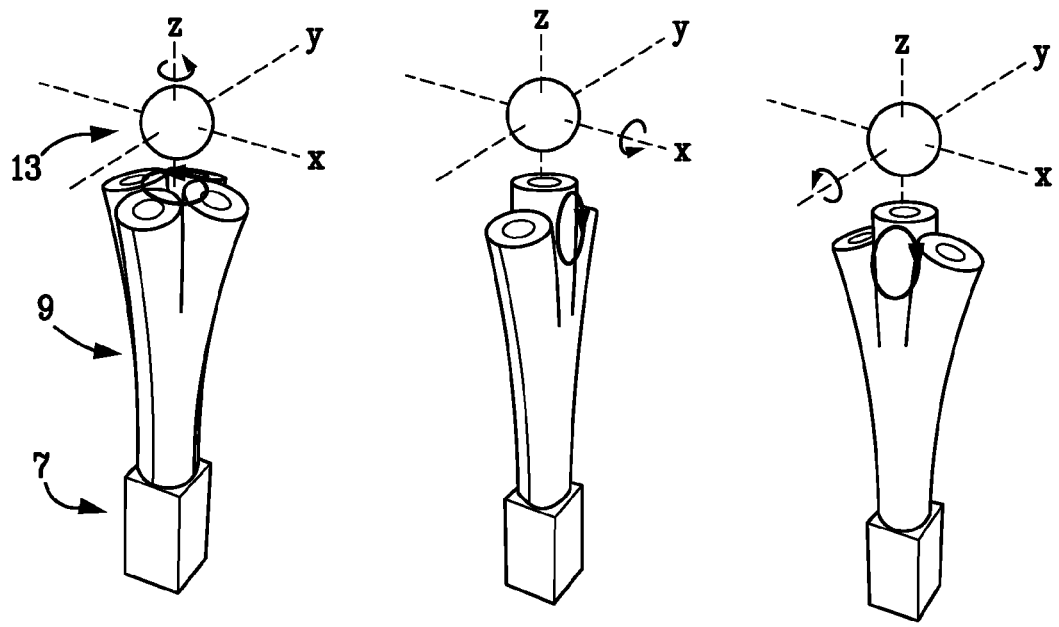

NAVIGABLE SYSTEM FOR CATHETER BASED ENDOVASCULAR NEUROSURGERY

CROSS-REFERENCE TO RELATED APPLICATIONS

This application is the National Stage of International Application No. PCT/AU2010/001136, filed Sep. 3, 2010, which claims the benefit of Australian Application No. 2009904281, filed Sep. 3, 2009, the disclosures of which are incorporated herein by reference in their entireties.

FIELD OF THE INVENTION

The present invention is generally directed to medical devices, and in particular to a navigable system for use in surgery. The present invention will be described with reference to its application in catheter based endovascular neurosurgery. It is however to be appreciated that other applications of the present invention are also envisaged.

BACKGROUND TO THE INVENTION

In the treatment of cerebrovascular disorders such as intracranial aneurysms and arteriovenous malformations (AVMs), there are two options for treatment: a craniotomy or minimally-invasive surgery (MIS) using micro-catheters. In the case of an aneurysm, endovascular occlusion using detachable coils, deployed via a micro-catheter, has become the preferred method over clip ligation through craniotomy. This is due to the lower rates of inpatient mortality, shorter hospital stays and lower treatment costs associated with the less invasive method.

The effectiveness of this method, however, is limited by the inability of current micro-catheters to reach and adequately treat aneurysms. Studies on the deployment of Guglielmi detachable coils (GDC), for example, revealed that 38 per cent of failures are the direct result of the inability to catheterise the aneurysm.

Catheters with variable distal ends are becoming increasingly popular, and are available in a myriad of configurations including mechanical tension-wire, electrically controlled memory-shape alloy and remote magnetic field navigation. All of these catheters, however, are limited to regions of the vasculature significantly greater than 1 mm in scale. This is due to their complexity of construction and their inability to navigate tight radius bends, which are synonymous with the neurovascular system. GDC procedures demand the ability to access regions of the vasculature as low as 350 µm in diameter.

In the first step of such catheter-based endovascular neurosurgery, a guidewire is inserted to just beyond the injured location. To reach the location, the guidewire must be pushed past the tortuous passage in the carotid artery at the base of the skull, and several Y-junctures must be navigated to reach even the most proximal locations within the brain. Indeed, roughly 85% of the brain cannot be reached with current technology. Guidewires are simply pushed back and forth repeatedly by the surgeon while viewed via x-ray to hopefully pass into the desired location. No rotation of the guidewire is possible, and only a few Y-junctions may be passed with the guidewire before too much friction risks rupture of the arteries near these junctures. Once the guidewire is correctly positioned, a micro-catheter is introduced over the guidewire to the injured location.

SUMMARY OF THE INVENTION

It would be advantageous to be able to provide a means for allowing the travel of a guidewire or micro-catheter utilised in catheter based endovascular neurosurgery to be navigated through the vasculature of the brain or other region of the body.

With this in mind, according to one aspect of the present invention, there is provided a navigable system for catheter based endovascular neurosurgery including:

a micro-motor including a piezoelectric actuator mounted to a free end of a guidewire or micro-catheter, the piezoelectric actuator including a piezoelectric element, and an elongate transducer mounted on the piezoelectric element and extending therefrom, the transducer being formed from an asymmetric hollow member, and an end member located at a free end of the transducer;

wherein electrical excitation of the piezoelectric element induces one or both orthogonal flexural and axial vibration modes within the transducer, the coupling of the induced vibration modes thereby resulting in rotation of the end member with three degrees of freedom (DOF).

The guidewire or micro-catheter used for catheter based endovascular neurosurgery may typically have a diameter of 350 microns. The micro-motor may therefore preferably have a maximum diameter equal to or less than the diameter of the guidewire or micro-catheter.

The transducer may be formed from a hollow cylindrical member having one or more grooves, pits, indentations, raised portions, cuts or apertures provided asymmetrically on an outer surface of the transducer to thereby provide said asymmetry.

It has been found that the asymmetry of the transducer helps to increase the amplitude of a flexural vibration mode in the transducer. It also aids in aligning the resonance frequency of said flexural mode with the resonance frequency of the axial vibration mode, thereby enabling motion suitable for motor operation. The coupling of the flexural and axial vibration mode allows vibration of the free end of the transducer with three degrees of freedom (DOF). The vibration may be or include a combination of vibration about an elongate axis of the transducer as well as about orthogonal axes extending lateral relative to the elongate axis thereof, with a difference in the phase of the vibrations such that elliptical motion about an arbitrary axis may be obtained.

At least one flagella may be secured to and extend from the end member. Preferably up to four flagellas may be provided. These flagellas assist in the propulsion and stabilization of the navigable system.

The end member may include a ball rotor mounted at the free end of the transducer and driven for rotation and translation with three DOF by the piezoelectric actuator as a consequence of such motion described prior. The end member may also include an elongate arm extending from the ball rotor and may be rotated and/or directed in different directions by controlling the motion of the ball rotor.

In order to allow the micro-motor to be controlled such that only small incremental adjustments can be made to the angular displacement of the end member, pulse width modulation (PWM) may be used to control the micro-motor.

According to another aspect of the present invention, there is provided a method of conducting catheter basal endovascular neurosurgery using a navigable system as described above.

In the navigable system according to the present invention, the end member can be rotated about its axis to assist in the propulsion of the guidewire system or micro-catheter, and also allows angular displacement of the end member relative to the guidewire or micro-catheter for steering within the vasculature. The micro-motor may have a diameter in the 1-500 micron range to facilitate its use in catheter based endovascular neurosurgery. In applications where the micro-motor is used with a micro-catheter, a cannulus, ie passage, may pass through the motor through to the passage within the micro-catheter.

BRIEF DESCRIPTION OF THE DRAWINGS

It will be convenient to further describe the invention with reference to the accompanying drawings which illustrate a preferred embodiment of the present invention. Other embodiments are possible, and consequently the particularity of the accompanying drawings is not to be understood as superseding the generality of the preceding description of the invention.

In the drawings:

FIG. 1(a) to (d) is a detailed view of the navigable guidewire system according to the present invention.

FIG. 2(a) to (c) shows the different flexural modes of the piezoelectric actuator according to the present invention.

DETAILED DESCRIPTION OF THE INVENTION

Figure 3:
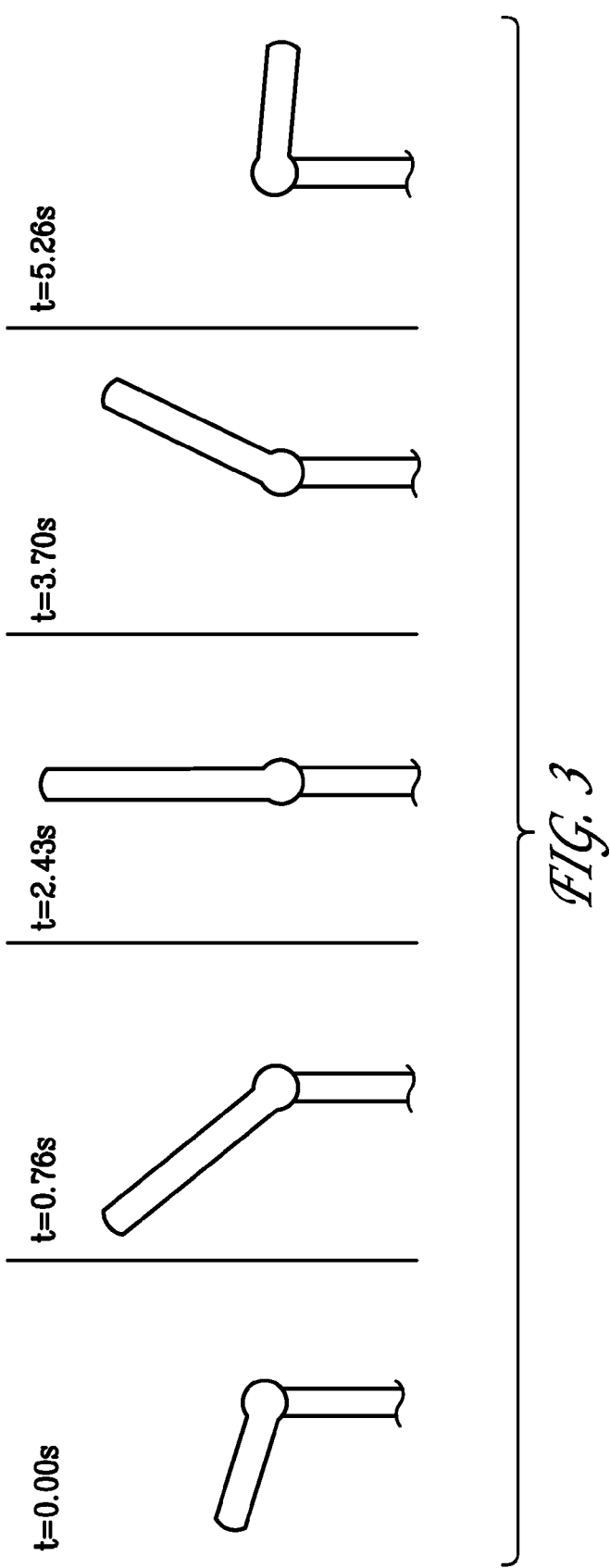
FIG. 3 are photos showing movement of the system according to the present invention.

The navigable system according to the present invention can be used for either a guidewire or a micro-catheter used in catheter based endovascular neurosurgery. The following example relates to its use on a guidewire.

Referring initially to FIG. 1, the navigable guidewire system according to the present invention includes a guidewire 2 upon which is mounted a micro-motor 3 having a piezoelectric actuator 5. The piezoelectric actuator 5 includes a piezoelectric element 7 secured to the end of the guidewire 2, and upon which is mounted an elongate transducer 9 in the form of a hollow cylinder. The micro-motor further includes ball rotor 13 mounted on the tip of the transducer 9 as shown in FIG. 1(b) to (d). An elongate member 15 extends from the ball rotor 13. The transducer 9 has one or more grooves or pits 17 provided in its outer surface to provide an asymmetry in the transducer, the effect of which is to allow flexural as well as axial vibration modes to be induced within the transducer at the same excitation frequency, necessary for operation. Further, this asymmetry is designed to increase the amplitude of vibration at the juncture with the rotor to improve performance of the motor.

FIGS. 1(b) to (c) show the configuration of the micro-motor 3 during use with the ball rotor 13 in contact with the transducer 9. At least the ball rotor 13 is formed from magnetic or magnetised material to thereby allow physical contact to be maintained with the transducer 9. One to four flagellas 19 may be secured to and extend from the end member 15. These flagellas, which assist in the propulsion and stabilization of the navigable system may be made from 5 μm Kevlar thread for example.

The micro-motor 3 may drive the end member 15 for rotation as shown in

FIG. 1(c) to assist in the propulsion of the guidewire. The micro-motor 3 may also direct the end member 15 at differing angular displacements to allow steering of the guidewire as shown in FIG. 1(d).

FIG. 2 shows in more detail of the different vibration modes that can be induced in the transducer 9.

The generation of motion from the resonant piezoelectric actuator 5 is based on the subjection of the transducer 9 to one or more periodic excitation(s). These periodic excitations at a resonance of the structure force the transducer 9 to oscillate about its mean position. Depending on the shape of such vibrational modes and the actuator's geometry, various output motions including translation and rotation may be realised.

The micro-motor 3 for the guidewire system according to the present invention drives the ball rotor 13 for rotation about different axes. Rotation can be generated about each of the transverse axes (x and y) via the coupling of a flexural vibrational mode with an axial mode within the transducer 9 (FIGS. 2(b) and 2(c)). In addition, rotation about the longitudinal axis (2) can be achieved via the coupling of two flexural vibrational modes (FIG. 2(a)). In order to realise these rotation schemes, each vibrational mode must be excited with a quarter wavelength phase difference to the other. That is, in FIGS. 2(b) and 2(c) the forcing function for the axial resonance must have a 90-degree phase shift from that of the flexural resonance. By altering which of the two forcing functions leads in phase, the rotation about any axis may be reversed. The net result is three DOF reversible rotation, whereby rotation is present about two orthogonal transverse axes (x and y) and about one longitudinal axis (z). The piezoelectric element 7 is used to force these vibrational tendencies to appear within the transducer 9.

Clinical tests have now been conducted of the guidewire system using a silicone model of the neurovasculature.

The micro-motor 3 needs to be controlled to allow surgeons to make small, incremental adjustments of the ball rotor angle for steering. This can be achieved using pulse width modulation (PWM), a control method that allows the input power to the motor to be digitally pulsed rather than continuously supplied. By varying the duty of the signal, ratio of on time to off time, the speed and power of the micro-motor 3 can be controlled. In addition, if a small step in the ball rotor 13 is required, a single pulse can be applied to the micro-motor 3. FIG. 3 shows the results of this control scheme used on the micro-motor 3, with reversible stepping of the micro-rotor about a transverse axis being realised. Here a length of nylon was attached to the ball rotor 13 for illustrative purposes.

Modifications and variations as would be deemed obvious to the person skilled in the art are included within the ambit of the present invention as claimed in the appended claims.

The invention claimed is:

1. A navigable system for catheter based endovascular neurosurgery including:
    a micro-motor including a piezoelectric actuator mounted to a free end of a guidewire or micro-catheter, the piezoelectric actuator including a piezoelectric element, and an elongate transducer mounted on the piezoelectric element and extending therefrom, the transducer being formed from an asymmetric hollow member, and an end member located at a free end of the transducer;
    wherein electrical excitation of the piezoelectric element induces one or both orthogonal flexural and axial vibration modes within the transducer, the coupling of the induced vibration modes thereby resulting in rotation of the end member with three degrees of freedom (DOF).

2. A navigable system according to claim 1 wherein the end member includes a ball rotor driven for rotation and translation in three DOF by the piezoelectric actuator.

3. A navigable system according to claim 2, wherein an elongate arm extends from and is moveable together with the ball rotor.

4. A navigable system according to claim 1, wherein the transducer is a hollow cylindrical member having one or more grooves, pits, indentations, raised portions, cuts or apertures provided asymmetrically on an outer surface of the transducer.

5. A navigable system according to claim 1, further including one or more flagellas secured to and extending from the end member.

6. A navigable system according to claim 1, wherein the micro-motor is controlled using pulse width modulation (PWM).

7. A method of conducting catheter based endovascular neurosurgery using a navigable system according to claim 1.

* * * * *